United States Patent [19]

Pero

[11] Patent Number: 5,204,241
[45] Date of Patent: Apr. 20, 1993

[54] GLUTATHIONE-S-TRANSFERASE MU AS A MEASURE OF DRUG RESISTANCE

[75] Inventor: Ronald W. Pero, New York, N.Y.

[73] Assignee: Oxi-Gene Inc., New York, N.Y.

[21] Appl. No.: 601,266

[22] Filed: Oct. 22, 1990

[51] Int. Cl.$^5$ .......................... C12Q 1/48; C12N 9/00
[52] U.S. Cl. ...................................... 435/15; 435/183
[58] Field of Search ................................ 435/15, 183

[56] References Cited

PUBLICATIONS

Leyland-Jones B. R. Antineoplastic Drug Sensitivity ... Chem. Abst. 114: 94779h Mar. 18, 1991.
Warholm M. Purification of a New GST Mu ... Biochem & Biophys Rsch Com 98 2: 512–519 Jan. 30, 1981.
Yusa K. Comparison of GST Activity Between ... Chem Abstracts, vol. 109, #13 109:104335y 1988.
Singh S. V. GST and Glutathione Peroxidases ... Chem. Abstracts 112:327t Jan. 1, 1990.
Morrow C. S. GST and Drug Resistance Chem. Abst. 112: 171572y May 7, 1990.
Begleiter A. Activity of Quinone Alkylating ... Chem. Abst. 113:70708n Aug. 27, 1990.
Seidegard, Janeric, Characterization of Soluble GST Activity ... Biochem. Pharm. 33 19: 3053–3058 1984.
Seidegard J. Hereditary Differences in the Expression ... Proc. Natl. Acad. Sci. USA 85:7293–7297 1988.
Peters W. H. M. Immunodetection with a Monoclonal Antibody ... Biochem. Pharm. 39 3:591–597 Jan. 1, 1990.
Johnston et al, J. Nat. Can. Inst., vol. 82, No. 9: 776–779 (1990).
Seidegard et al, Carcinogenesis, vol. 6, No. 8: 1211–1216 (1985).
Seidegard et al, J. Biochem. 246: 783–785 (1987).

*Primary Examiner*—John W. Rollins
*Assistant Examiner*—Ralph Gitomer
*Attorney, Agent, or Firm*—Cooper & Dunham

[57] ABSTRACT

It has been discovered that by determining or measuring a person's glutathione-s-transferase (GST) mu activity one can determine or measure the individual's resistance to drugs, particularly to chemotherapeutic drugs. Approximately 50% of the human population exhibit substantially no GST mu activity, with the remaining 50% showing GST mu activity. This remaining 50% of the population accordingly, when treated with drugs, such as a chemotherapeutic drug for cancer therapy, show less effective response to the drug therapy than the other 50% of the population which have substantially no GST mu activity, since GST mu tends to deactivate drugs. Accordingly, a person having GST mu activity would exhibit drug resistance and would not benefit as much by or be as good a candidate for cancer chemotherapy as a person who has no GST mu activity.

13 Claims, 1 Drawing Sheet

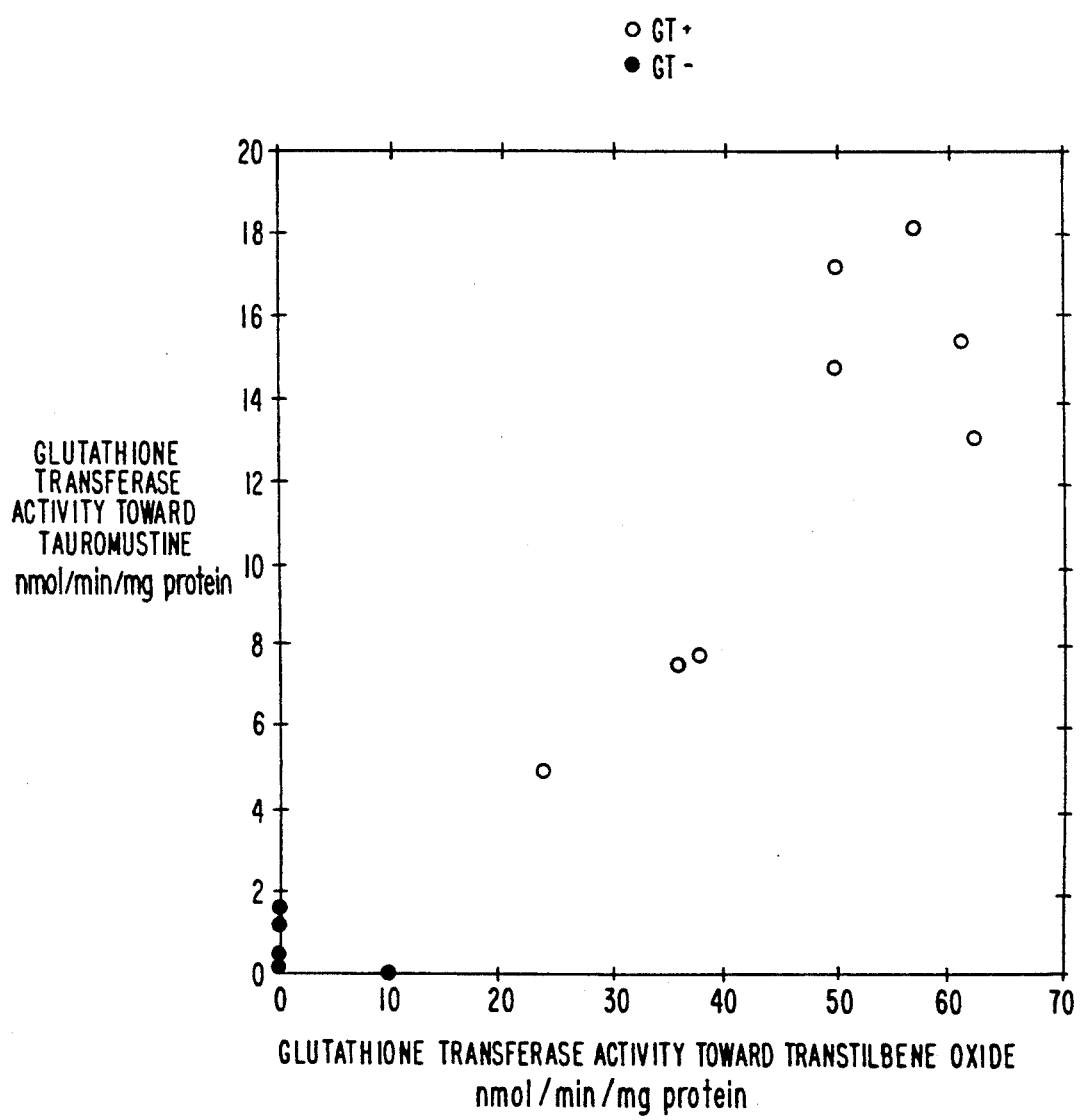

GLUTATHIONE-S-TRANSFERASE MU AS A MEASURE OF DRUG RESISTANCE

BACKGROUND OF THE INVENTION

Glutathione-s-transferases (GSTs) are a group of multi-functional proteins which play an important role in the biotransformation of many different biologically active compounds, including agents which damage DNA, such as chemotherapeutic drugs, see Mannervik, B., *Adv. Enzymol. Relat. Areas Mol. Biol.* 57: 357–417 (1985). Indeed, it is known that GSTs are usually associated with the detoxification by conjugation of genotoxic and cytotoxic xenobiotic electrophiles derived from drugs, carcinogens and environmental pollutants, see Glutathione transferases; H. Sies and B. Ketterer (eds.), *Glutathione Conjugation. Academic Press, New York*, pp. 74–135 (1988).

On the basis of physical and immunological properties and substrate specificities and protein structure, the human GSTs have been divided into three distinct classes, named alpha, mu and pi, see Mannervik B., et al, *Proc. Natl. Acad. Sci. U.S.A.* 82: 7202–7206 (1985).

It is an object of this invention to employ glutathione-s-transferase activity as a measure of drug resistance.

How this and other objects of this invention are achieved will become apparent in the light of the accompanying disclosure, including the drawing which graphically illustrates the subject invention. In at least one embodiment of the practices of this invention at least one of the objects of this invention will be achieved.

Cellular reduced glutathione, i.e. the co-substrate for GSTs, and GST activity in general, i.e. total activity estimated using 1-chloro-3,4-dinitrobenzene (CDNB) as a substrate, has been shown to be involved in the mechanism of chemotherapeutic drug resistance, see Johnston et al, *J. Natl. Can. Inst.* 82: 776–779 (1990) and Lai, G-M, et al, *J. Natl. Can. Inst.* 81: 535–539 (1989).

Chemotherapeutic agents, such as chlorambucil cisplatin, nitrosoureas and other chemotherapeutic drugs that can damage DNA or other cellular macromolecules, such as RNA or protein, are electrophiles which can be conjugated with glutathione directly or indirectly via GST activity. Hence, high levels of glutathione and/or GST activity provide a mechanism of drug resistance because cells having high levels have increased opportunities to remove the drugs before the drugs can cause genotoxicity or cytotoxicity or other adverse effects. Heretofore, however, it has not been known whether any one of the known GST isozymes, either the alpha, pi or the mu class, is more specifically involved in conjugating chemotherapeutic drugs with glutathione.

BRIEF DESCRIPTION OF THE INVENTION

It has now been discovered, and it is the basis of this invention, that GST mu isozymes are specifically and preferentially involved in the metabolism of chemotherapeutic drugs. In accordance with this invention it has now been discovered that by measuring GST mu activity, one can estimate and/or measure an individual's resistance to chemotherapeutic drugs.

The mu class of GSTs are distinguished by having a high substrate specificity towards trans-stilbene oxide, see Seidegard, J.-E. et al, *Biochem. J.* 246: 783–785 (1987). About 50% of the human population lack GST mu because of a gene deletion, see Seidegard, J.-E and Pero, R. W., *Genet.* 69: 66–68 (1985) and Seidegard et al *Proc. Natl. Acad. Sci. U.S.A.* 85: 7293–7295 (1988). Individuals can be easily phenotyped for the presence (+) or absence (−) of GST Mu activity. Because GST mu activity represents at least 60% of the total GST activity in liver, see Warholm, M. et al, *Biochemistry* 22: 3610–3617 (1983), and since the liver is the main source of metabolism of xenobiotic substances, including chemotherapeutic drugs, and since GST mu has been shown to have high substrate specificity toward toxic agents, such as trans-stilbene oxide, benzopyrene 4,5-oxide and ethylene oxide, but little substrate specificity for other GST substrates, such as cis-stilbene oxide and 1-chloro-2,4-dinitrobenzene, see Seidergard, J.-E. et al, *Carcinogenesis* 6: 1121–1216) 1985, GST mu activity may be employed to estimate a genetic based sensitivity of individuals to metabolize chemotherapeutic drugs.

BRIEF DESCRIPTION OF THE DRAWING

The single FIGURE is a graph in which glutathione transferase activity toward tauromustine is plotted against glutathione transferase activity toward trans-stilbene oxide.

DETAILED DESCRIPTION OF THE INVENTION

The following example is illustrative of the practices of this invention. In the example tauromustine, a nitrosourea, a class of chemotherapeutic drugs, was metabolized to a much greater extent by human liver cytosols having GST mu activity than by human liver cytosols lacking GST mu activity. The data illustrated in the accompanying drawing teach that the presence (+) or absence (−) of GST mu can predict individual sensitivity to chemotherapeutic drugs, such as nitrosoureas, which damage DNA.

EXAMPLE

The importance of the GST-tSBO phenotype in influencing drug metabolism is indicated by the following. Tauromustine is a drug representative of the class of chemotherapeutic agents known as the nitrosoureas and has the structural formula:

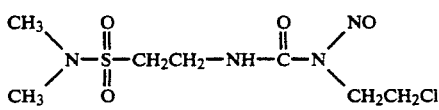

Human liver biopsies from ? 3 individuals were homogenized in 5 vol. of 0.25 M sucrose, centrifuged at 10,000 g for 15 minutes and then the resulting supernatant was re-centrifuged at 105,000 g for one hour. The 105,000 g supernatants were analyzed for glutathione transferase activity using trans-stilbene oxide (tSBO) and tauromustine as substrates. Metabolism of these substrates to glutathione conjugates was monitored by radiometric procedures involving differential organic solvent extraction, see Gill, S., Ota, J. and Hammock, B. D. *Anal. Biochem.* 131: 273–282 (1983), and high pressure liquid chromatography (HPLC).

The results are graphically presented in the accompanying drawing. When GST-tSBO activity in liver cytosols was 0–10 nmo/min/mg protein, the level of glutathione transferase activity toward tauromustine was also very low ranging from 0–2 nmol/min/mg protein. However, when there was easily detectable GST-tSBO activity, i.e. 25-65 nmol/min/mg proteins, there was also substantial metabolism of tuuromustine (i.e. 4-19 nmol/min/mg protein).

As mentioned hereinabove, there are at least three different classes of human glutathione transferases, the alpha, mu and pi classes. Each class is composed of several isozymes and GST-tSBO has been determined to be a distinct isozyme of the mu class. Hence, these data teach that the metabolism of nitrosoureas, such as are represented by tauromustine, is mainly carried out by GST-tSBO, identical to GST-mu, and not by the other isozymes of glutathione transferase. It follows then, since GST-tSBO activity has been shown to be under genetic control and to be absent in about 50% of the population, there would also be about 50 % of the population with a higher degree of resistance to chemotherapy, such as to chemotherapeutic drugs represented by the nitrosoureas.

The embodiment of this invention recognizes the prior knowledge that glutathione and total GST activity, usually measured with CDNB as substrate, can contribute to drug resistance. However, CDNB can serve as a substrate for all the GST ioszyme sub-groups (i.e. alpha, pi and mu classes), and it was not obvious or recognized that any single GST isozyme was contributing more than any other to drug metabolism. Moreover, the pi class of GST isozymes had been the only GST to be more directly implicated in chemotherapeutic drug resistance, see Moscow, J. A. and Cowan, K. H., J. Natl. Can. Inst. 80: 14-20 (1988) and even then, only in relation to reduced glutathione levels. In other words, the selective metabolism of a chemotherapeutic drug by GST pi isozymes, or any other GST other than GST mu, shown in Example 1, has not been demonstrated. This has implied that the substrate specificity of GSTs is very broad and the various classes of GSTs can metabolize drugs in a reasonably equal manner. Therefore, it was unexpected that GST mu isozymes could contribute so dramatically to chemotherapeutic drug resistance in individuals expressing GST -Mu activity compared to individuals lacking GST mu activity, even though both GST mu (+) and (−) individuals have other classes of GST activity present.

Although the expression of the GSTs is organ specific, the expression of GST mu is known to be controlled by genetic factors where about 50% of the population has no GST mu activity. None of the other human GSTs have been shown to be lacking in such a large portion of the population, nor have they been shown to have a high degree of substrate specificity controlled by genetic factors. The combination of these GST mu characteristics, together with the demonstrated selective metabolism of nitrosureas by GST mu show that the GST mu phenotype can be predictive of chemotherapeutic drug resistance via metabolism characterized by a selective conjugation with glutathione catalyzed or brought about by GST mu.

In the practices of this invention testing of a person's GST mu activity can be carried out by obtaining and testing the blood samples of the human to be tested as well as tissue or organ samples, such as the liver, colon, breast and adrenal glands. Particularly useful, from the point of view of convenience in carrying out the tests and determinations in accordance with this invention, would be to carry out the tests on the person's mononuclear leukocytes. All the tests would be carried out employing trans-stilbene oxide as the substrate for the glutathione transferase since transstilbene oxide is a specific substrate for glutathione transferase GST mu. The level of glutathione transferase activity towards trans-stilbene oxide would be measured as nmol/mn/mg protein and level of four (4), especially a level higher than eight (8), would be indicative that the person so tested for glutathione transferase mu activity would posses substantial drug resistance and would not be a good candidate for drug therapy or cancer chemotherapy and the like, even when the person so tested might evidence glutathione transferase activity of the GST alpha and pi classes.

Instead of using tSBO as a substrate to phenotype individuals for GST mu affinity and thus drug resistance, other ways of determining GST mu activity may be employed. For example the (+) or (−) GST mu activity can also be determined by using antibodies derived from purified GST mu or a DNA probe derived from or based on the GST mu gene.

All the above-cited publication references are herein incorporated and made part of this disclosure.

As will be apparent to those skilled in the art in the light of the foregoing disclosure, many modifications, alterations and substitutions are possible in the practices of this invention without departing from the spirit or scope thereof.

What is claimed is:

1. A method of determining the resistance of a human individual to a nitrosourcea which comprises determining the GST mu activity of the individual, to establish a measured value of the individual's GST mu activity, and comparing said measured value with a predetermined value, the presence of a GST mu activity above said predetermined value indicting that the individual is resistant to the nitrosourcea.

2. A method according to claim 1, wherein the determining step is performed using tSGO to measure the individual's GST mu activity.

3. A method according to claim 1, wherein the determining step is performed using an antibody to GST mu to measure the individual's GST mu activity.

4. A method according to claim 1, wherein the determining step is performed using a labeled DNA probe for the GST mu gene to measure the individual's GST mu activity.

5. A method according to claim 1, wherein the determining step is performed by testing liver tissue of the individual.

6. A method according to claim 1, wherein the determining step is performed by testing colon tissue of the individual.

7. A method according to claim 1, wherein the determining step is performed by testing breast tissue of the individual.

8. A method according to claim 1, wherein the determining step is performed by testing mononuclear leukocytes of the individual.

9. A method according to claim 2, wherein the determining step is performed by testing liver tissue of the individual.

10. A method according to claim 2 wherein the determining step is performed by testing mononuclear leukocytes of the individual.

11. A method according to claim 1 wherein to said measured value of GST mu activity is measured towards tSBO, nmol/min/mg protein, and said predetermined value is 4 or above.

12. A method according to claim 1 wherein said nitrosourea is tauromustine.

13. A method of determining the resistance of a human individual to tauromustine, comprising determining GST mu activity of liver tissue of the individual using tSBO, to establish a measured value of said activity expressed in nmol/min/mg protein and comparing said measured value with a value of 4, a measured value above 4 indicating that the individual is resistant to tauromustine.

* * * * *